(12) United States Patent
Madabhushi et al.

(10) Patent No.: US 11,540,796 B2
(45) Date of Patent: Jan. 3, 2023

(54) PREDICTION OF RISK OF POST-ABLATION ATRIAL FIBRILLATION BASED ON RADIOGRAPHIC FEATURES OF PULMONARY VEIN MORPHOLOGY FROM CHEST IMAGING

(71) Applicants: Case Western Reserve University, Cleveland, OH (US); The Cleveland Clinic Foundation, Cleveland, OH (US)

(72) Inventors: Anant Madabhushi, Shaker Heights, OH (US); Michael LaBarbera, Cleveland Heights, OH (US); Thomas Atta-Fosu, Cleveland Heights, OH (US); Mina Chung, Shaker Heights, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 811 days.

(21) Appl. No.: 16/363,203

(22) Filed: Mar. 25, 2019

(65) Prior Publication Data
US 2019/0357869 A1     Nov. 28, 2019

Related U.S. Application Data

(60) Provisional application No. 62/675,358, filed on May 23, 2018.

(51) Int. Cl.
*A61B 6/00* (2006.01)
*G16H 50/30* (2018.01)
(Continued)

(52) U.S. Cl.
CPC .............. *A61B 6/503* (2013.01); *A61B 6/032* (2013.01); *A61B 6/463* (2013.01); *G16H 50/30* (2018.01);
(Continued)

(58) Field of Classification Search
CPC ......... A61B 6/503; A61B 6/032; A61B 6/463; A61B 5/361; A61B 6/469; A61B 6/5217;
(Continued)

(56) References Cited

U.S. PATENT DOCUMENTS

| | | | |
|---|---|---|---|
| 2016/0196647 A1* | 7/2016 | Madabhushi | .... G01R 33/34084 382/131 |
| 2018/0078312 A1* | 3/2018 | Trayanova | ............. G16H 30/20 |

OTHER PUBLICATIONS

Karnik et al . 2012 34th Annual International Conference of the IEEE EMBS p. 5562-5565 (Year: 2012).*

(Continued)

*Primary Examiner* — Colin T. Sakamoto
*Assistant Examiner* — Patrick M Mehl
(74) *Attorney, Agent, or Firm* — Eschweiler & Potashnik, LLC (57) ABSTRACT

Embodiments discussed herein facilitate generation of a prognosis for recurrence or non-recurrence of atrial fibrillation (AF) after pulmonary vein isolation (PVI). A first set of embodiments discussed herein relates to training of a machine learning classifier to determine a prognosis for AF after PVI based on radiographic images, alone or in combination with clinical features. A second set of embodiments discussed herein relates to determination of a prognosis for a patient for AF after PVI based on radiographic images, alone or in combination with clinical features.

20 Claims, 8 Drawing Sheets
(2 of 8 Drawing Sheet(s) Filed in Color)

(51) Int. Cl.
*A61B 6/03* (2006.01)
*A61B 18/00* (2006.01)
*G16H 50/20* (2018.01)
*G06N 20/00* (2019.01)
*G16H 10/60* (2018.01)
*G16H 30/40* (2018.01)
*A61B 5/361* (2021.01)

(52) U.S. Cl.
CPC .............. *A61B 5/361* (2021.01); *A61B 6/469* (2013.01); *A61B 6/5217* (2013.01); *A61B 6/54* (2013.01); *A61B 2018/00351* (2013.01); *A61B 2018/00577* (2013.01); *G01N 2800/52* (2013.01); *G06N 20/00* (2019.01); *G06T 2207/30048* (2013.01); *G16H 10/60* (2018.01); *G16H 30/40* (2018.01); *G16H 50/20* (2018.01)

(58) Field of Classification Search
CPC ............ A61B 6/54; A61B 2018/00351; A61B 2018/00577; A61B 5/4842; A61B 5/7267; A61B 5/7275; A61B 34/10; A61B 5/055; A61B 2576/023; G16H 50/30; G16H 10/60; G16H 30/40; G16H 50/20; G16H 20/00; G01N 2800/52; G06N 20/00; G06N 5/003; G06N 7/005; G06N 20/10; G06N 20/20; G06T 2207/30048
See application file for complete search history.

(56) References Cited

OTHER PUBLICATIONS

Letsas et al. 2009 Europace 11:158-163 (Year: 2009).*
Siontis et al. 2015 Circ Cardiovasc Imaging 8:e003020 10 pages (Year: 2015).*
Varela et al .2017 Frontiers in Physiology 8:68 12 pages (Year: 2017).*
Buist et al. 2016 J. Cardiovascular Computed Tomography 10:251-257 (Year: 2016).*
Dries et al. 1998 JACC 321:695-703 (Year: 1998).*

* cited by examiner

FIG. 8

PREDICTION OF RISK OF POST-ABLATION ATRIAL FIBRILLATION BASED ON RADIOGRAPHIC FEATURES OF PULMONARY VEIN MORPHOLOGY FROM CHEST IMAGING

CROSS REFERENCE TO RELATED APPLICATIONS

This application claims the benefit of U.S. Provisional Patent Application No. 62/675,358 filed May 23, 2018, entitled "RADIOGRAPHIC FEATURES OF PULMONARY VEINS MORPHOLOGY FROM CHEST CT PREDICTS RISK OF POST-ABLATION ATRIAL FIBRILLATION", the contents of which are herein incorporated by reference in their entirety.

BACKGROUND

Atrial fibrillation (AF) is the most common sustained arrhythmia, affecting 1-2% of the population. Although endovascular pulmonary vein isolation (PVI) may temporarily reduce symptoms in patients failing medical management, recurrence rates are high and identifying patients likely to have successful outcomes remains elusive. Pulmonary vein morphology and left atrial size have been previously identified as radiographic markers for AF, but have not been assessed for PVI outcome.

BRIEF DESCRIPTION OF THE DRAWINGS

The patent or application the contains at least one drawing executed in color. Copies of this patent or patent application publication with color drawing(s) will be provided by the Office upon request and payment of the necessary fee.

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments can employ techniques discussed herein for prediction of recurrence or non-recurrence of atrial fibrillation (AF) following endovascular pulmonary vein isolation (PVI) via a machine learning classifier trained on radiological (e.g., CT (Computed Tomography), etc.) and clinical features that have been identified as distinguishing between recurrence and non-recurrence. In various embodiments, radiographic features employed by various embodiments can comprise pulmonary vein and left atrial morphometric features.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
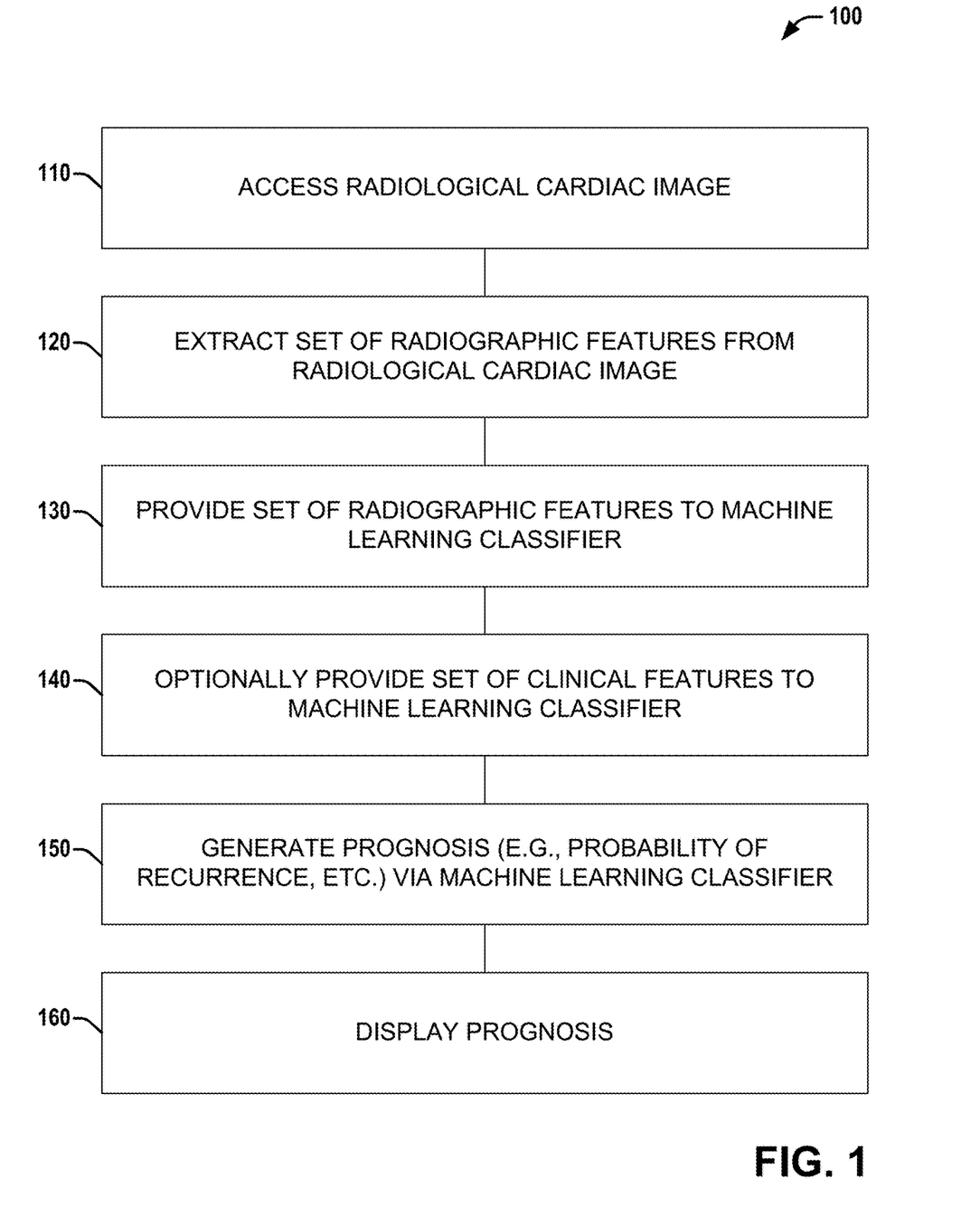
FIG. 1 illustrates a diagram of a first example flow of a method or set of operations that employs a machine learning classifier to generate a prognosis of recurrence or non-recurrence of AF after PVI based on morphometric features of a radiological image in combination with clinical features, according to various embodiments discussed herein.

Various embodiments can employ techniques discussed herein to facilitate determination of a prognosis of recurrence or non-recurrence of atrial fibrillation (AF) following endovascular pulmonary vein isolation (PVI). Referring to FIG. 1, illustrated is a diagram showing a first example flow of a method or set of operations 100 that employs a machine learning classifier to generate a prognosis of recurrence or non-recurrence of AF after PVI based on morphometric features of a radiological image in combination with clinical features, according to various embodiments discussed herein.

The set of operations 100 can comprise, at 110, accessing a radiological cardiac image (e.g., chest CT (Computed Tomography), MRI (Magnetic Resonance Imaging), ultrasound, PET (Positron-Emission Tomography), SPECT (Single-Photon Emission Computed Tomography), etc.). The accessed radiological cardiac image can be stored in memory locally or remotely, and can be obtained via a medical imaging device one of concurrently with method 100 (e.g., via a medical imaging device implementing method 100) or prior to method 100.

The set of operations 100 can further comprise, at 120, extracting a set of radiographic features from the radiological cardiac image (e.g., chest CT, etc.). In various embodiments, the set of radiographic features can comprise M (for M a positive integer, e.g., 5, or a greater or lesser number) features that have been identified (e.g., via an algorithm or measure such as RF, t-test, Wilcoxon, mRMR, etc.) as the M most distinguishing or discriminating radiographic features for recurrence versus non-recurrence of AF post-PVI. Extraction of features can be performed in an automated manner or semi-automated manner (e.g., via measurements automatically obtained based on user defined points, etc.).

The set of operations 100 can further comprise, at 130, providing the set of radiographic features to a machine learning classifier that has been trained to distinguish between recurrent and non-recurrent AF after PVI based at least in part on values of those radiographic features.

The set of operations 100 can optionally comprise, at 140, providing a set of clinical features to the machine learning classifier. In various embodiments, the set of clinical features can comprise N (for N a positive integer, e.g., 5, or a greater or lesser number) features that have been identified (e.g., via an algorithm or measure such as RF, t-test, Wilcoxon, mRMR, etc.) as the N most distinguishing or discriminating clinical features for recurrence versus non-recurrence of AF post-PVI.

The set of operations 100 can further comprise, at 150, generating a prognosis via the machine learning classifier based on the radiographic features and optional clinical features. In various embodiments, the prognosis can comprise one or more of a most likely prognostic outcome (e.g., as determined based on the radiological and/or clinical features, etc.) such as recurrence or non-recurrence; a probability or confidence associated with a most likely prognostic outcome; and/or associated probabilities/confidences associated with each of a plurality of prognostic outcomes (e.g., recurrence, non-recurrence, etc.).

The set of operations 100 can further comprises, at 160, displaying the prognosis, and can optionally comprise displaying one or more of the set of radiographic features, the set of clinical features, or the radiological cardiac image. Displaying the prognosis and optionally displaying one or more of the set of radiographic features, the set of clinical features, or the radiological cardiac image can comprise displaying the prognosis and optionally displaying one or more of the set of radiographic features, the set of clinical features, or the radiological cardiac image on a computer monitor, a smartphone display, a tablet display, or other displays. Displaying the prognosis and optionally displaying one or more of the set of radiographic features, the set of clinical features, or the radiological cardiac image can also comprise printing the prognosis and optionally printing one or more of the set of radiographic features, the set of clinical features, or the radiological cardiac image. Displaying the prognosis and optionally displaying one or more of the set of radiographic features, the set of clinical features, or the radiological cardiac image can also comprise controlling a recurrence prediction system, a personalized medicine system, a monitor, or other display, to display operating parameters or characteristics of a machine learning classifier, during at least one of training and testing of the machine learning classifier, or during clinical operation of the machine learning classifier. By displaying the prognosis and optionally displaying one or more of the set of radiographic features, the set of clinical features, or the radiological cardiac image, example embodiments provide a timely and intuitive way for a human medical practitioner to more accurately classify AF as more likely to experience recurrence post-PVI, or less likely to experience recurrence post-PVI, thus improving on existing approaches to predicting recurrence. Embodiments may further display operating parameters of the machine learning classifier.

Figure 2:
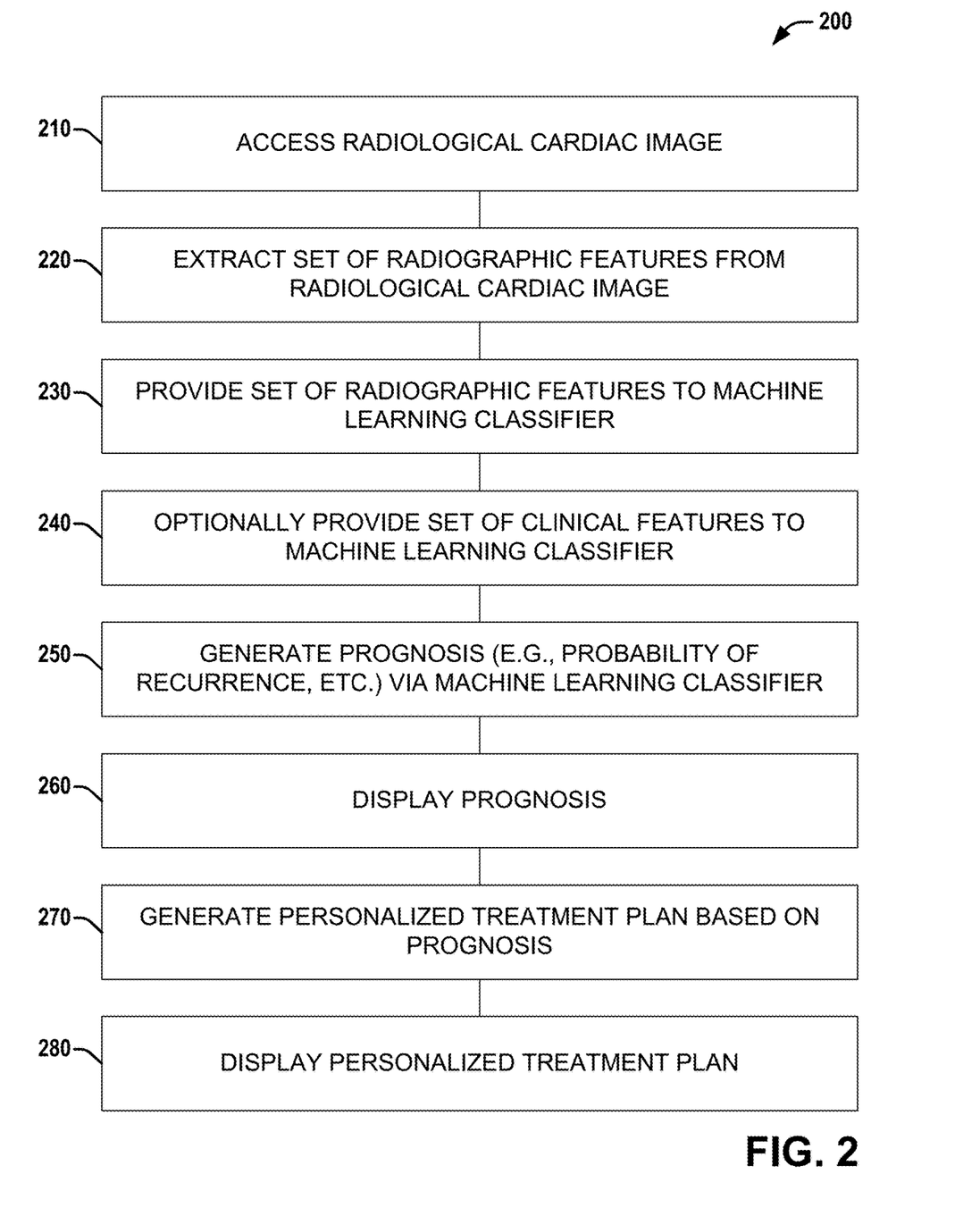
FIG. 2 illustrates a diagram of a second example flow of a method or set of operations that employs a machine learning classifier to generate a prognosis of recurrence or non-recurrence of AF after PVI based on morphometric features of a radiological image in combination with clinical features, according to various embodiments discussed herein.

Referring to FIG. 2, illustrated is a diagram showing a second example flow of a method or set of operations 200 that employs a machine learning classifier to generate a prognosis of recurrence or non-recurrence of AF after PVI based on morphometric features of a radiological image in combination with clinical features, according to various embodiments discussed herein. Method or set of operations 200 is similar to method or set of operations 100, but can include additional operations and/or features.

The set of operations 200 can comprise, at 210 through 260, operations substantially similar to operations 110 through 160 of set of operations 100.

The set of operations 200 can further comprise, at 270, generating a personalized AF treatment plan. The personalized AF treatment plan can be generated based, at least in part, on the prognosis and optionally on one or more of the set of radiographic features, the set of clinical features, or the radiological cardiac image. The personalized AF treatment plan may be generated for the patient of whom the radiological cardiac image was acquired based, at least in part, on the prognosis and optionally on one or more of the set of radiographic features, the set of clinical features, or the radiological cardiac image. Defining a personalized AF treatment plan facilitates delivering a particular treatment that will be therapeutically active to the patient, while minimizing negative or adverse effects experienced by the patient. For example, the personalized AF treatment plan may suggest a surgical treatment, may define a pharmaceutical agent dosage or schedule and/or other recommendations for AF management, for a patient, wherein the specific recommendation can depend on whether or not the patient is likely to experience recurrence. Generating the personalized AF treatment plan includes acquiring electronic data, reading from a computer file, receiving a computer file, reading from a computer memory, or other computerized activity not practically performed in the human mind.

The set of operations 200 can further comprise, at 280, displaying the personalized AF treatment plan according to embodiments described herein.

Figure 3:
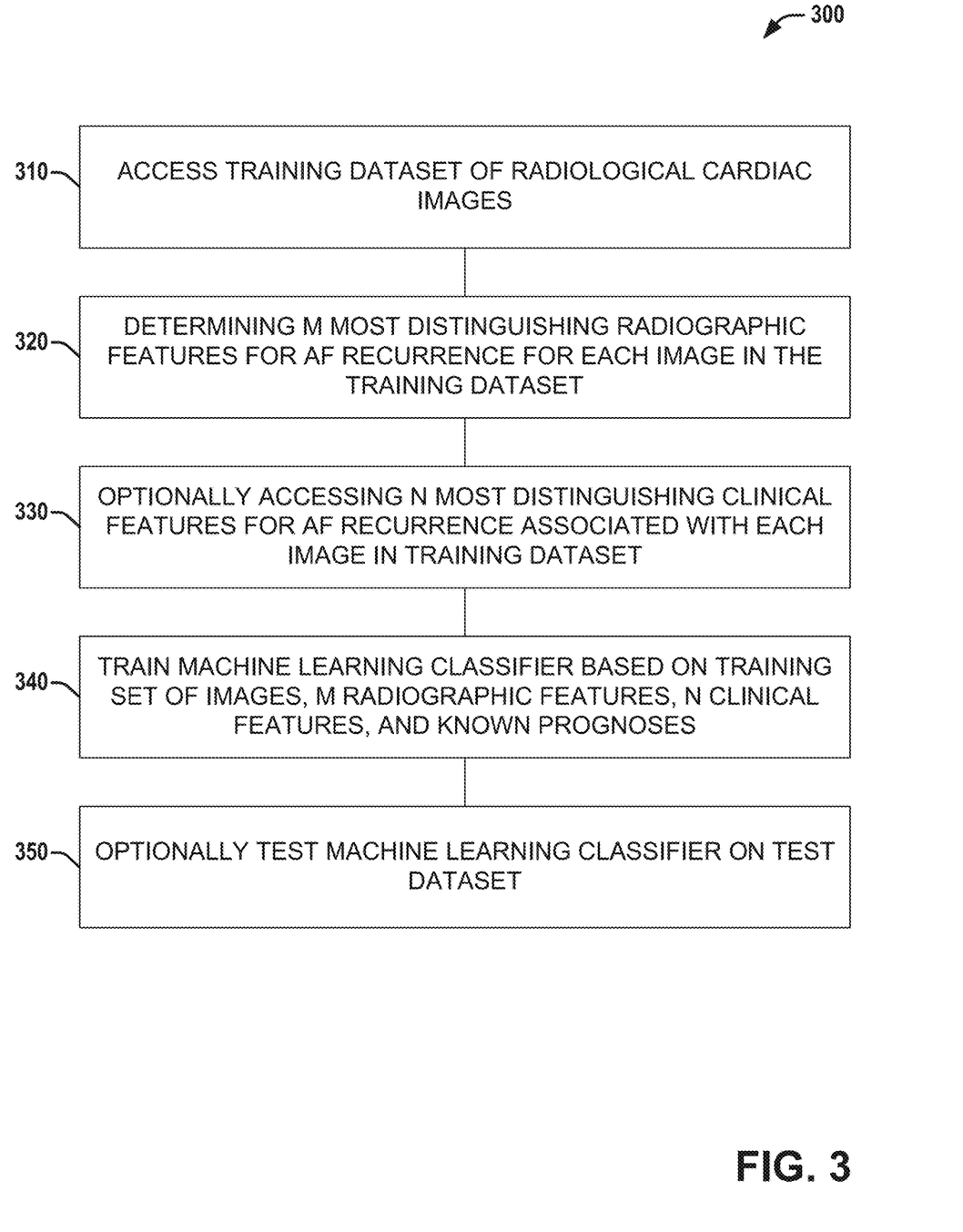
FIG. 3 illustrates a diagram of an example flow of a method or set of operations that facilitates training of a machine learning classifier to generate prognoses of recurrence or non-recurrence of AF via PVI based on morphometric features of radiological image(s) in combination with clinical features, according to various embodiments discussed herein.

Referring to FIG. 3, illustrated is a diagram showing an example flow of a method or set of operations 300 that facilitates training of a machine learning classifier to generate prognoses of recurrence or non-recurrence of AF via PVI based on morphometric features of radiological image (s) in combination with clinical features, according to various embodiments discussed herein.

The set of operations 300 can comprise, at 310, accessing a training dataset of radiological cardiac images. As explained in greater detail herein, the training dataset can comprise a plurality of cardiac images comprising a positive set that is associated with a first classification (e.g., recurrence or non-recurrence of AF post-PVI) and a negative set that is associated with a different second classification (e.g., non-recurrence or recurrence, respectively, of AF post-PVI).

The set of operations 300 can further comprise, at 320, determining, for each image in the training dataset, values for that image for each of the M (for M a positive integer) most distinguishing radiographic features for post-PVI recurrence of AF. The M most distinguishing radiographic features can be determined via any of a variety of algorithm or measures (e.g., RF, t-test, Wilcoxon, mRMR, etc.).

The set of operations 300 can further comprise, at 330, accessing, for each image in the training dataset, values for a patient associated with that image for each of the N (for N a positive integer) most distinguishing clinical features for post-PVI recurrence of AF. The N most distinguishing clinical features can be determined via any of a variety of algorithm or measures (e.g., RF, t-test, Wilcoxon, mRMR, etc.).

The set of operations 300 can further comprise, at 340, training a machine learning classifier (e.g., SVM (Support Vector Machine), LDA (Linear Discriminant Analysis) classifier, QDA (Quadratic Discriminant Analysis classifier), DLDA (Diagonal Line Discriminant Analysis) classifier, RF (Random Forest) classifier, CNN (Convolutional Neural Network) classifier, etc.) based on the training dataset, and, for each image in the training dataset, the values of the M radiographic features for that image, the values of the N clinical features associated with that image, and a known prognosis (e.g., recurrence or non-recurrence of AF post-PVI) associated with that image. Based on the training dataset, and, for each image in the training dataset, the values of the M radiographic features for that image, the values of the N clinical features associated with that image, and a known prognosis (e.g., recurrence or non-recurrence of AF post-PVI) associated with that image, the classifier can determine classes for recurrence and non-recurrence, and probability of recurrence or non-recurrence for associated feature vectors (e.g., comprising M values of radiographic features and optionally N values of clinical features).

The set of operations 300 can optionally comprise, at 350, testing the machine learning classifier on a test dataset comprising radiological cardiac images for which prognoses are known (e.g., in a manner similar to set of operations 100 or 200, additionally comprising comparing a generated prognosis with the known prognosis). In this manner, the ability of the machine learning classifier to correctly classify radiological cardiac images (and optionally, associated clinical features) based on recurrence or non-recurrence of AF post-PVI can be estimated.

Training the machine learning classifier can also comprise determining which radiographic and/or clinical features are most discriminative in distinguishing recurrence or non-recurrence of AF post-PVI and/or determining the optimal combination of parameters used in the computation of the probability (e.g., the angle between right pulmonary veins, the angle of left inferior pulmonary vein entry into the left atrium, etc.) can best separate a positive class from a negative class (e.g., a recurrent class from a non-recurrent class, or vice versa).

Techniques and aspects of various embodiments are further explained below, in connection with an example embodiment that facilitates determination of prognoses of recurrence or non-recurrence of post-ablation atrial fibrillation.

Example Use Case: Radiographic Features of Pulmonary Vein Morphology from Chest CT Predicts Risk of Post-Ablation Atrial Fibrillation An example embodiment trained a classifier to predict recurrence or non-recurrence of atrial fibrillation (AF) after endovascular pulmonary vein isolation (PVI), based on example cases of recurrent and non-recurrent AF. A retrospective review of PVI procedures from 2014-2016 excluding prior PVI or valve surgery revealed 314 cases. 154 had pre-PVI CT imaging and clinician-assessed PVI outcome recorded in the EMR at follow-up, with 50 cases diagnosed with recurrent AF within 3 months to 1 year. 50 non-recurrent cases were randomly selected to produce a balanced dataset for analysis (n=100). Radiographic features were obtained characterizing left atrium size, pulmonary vein morphology, and angle of vein entry into the left atrium using Syngo.Via (©Siemens Healthcare).

Figure 4:
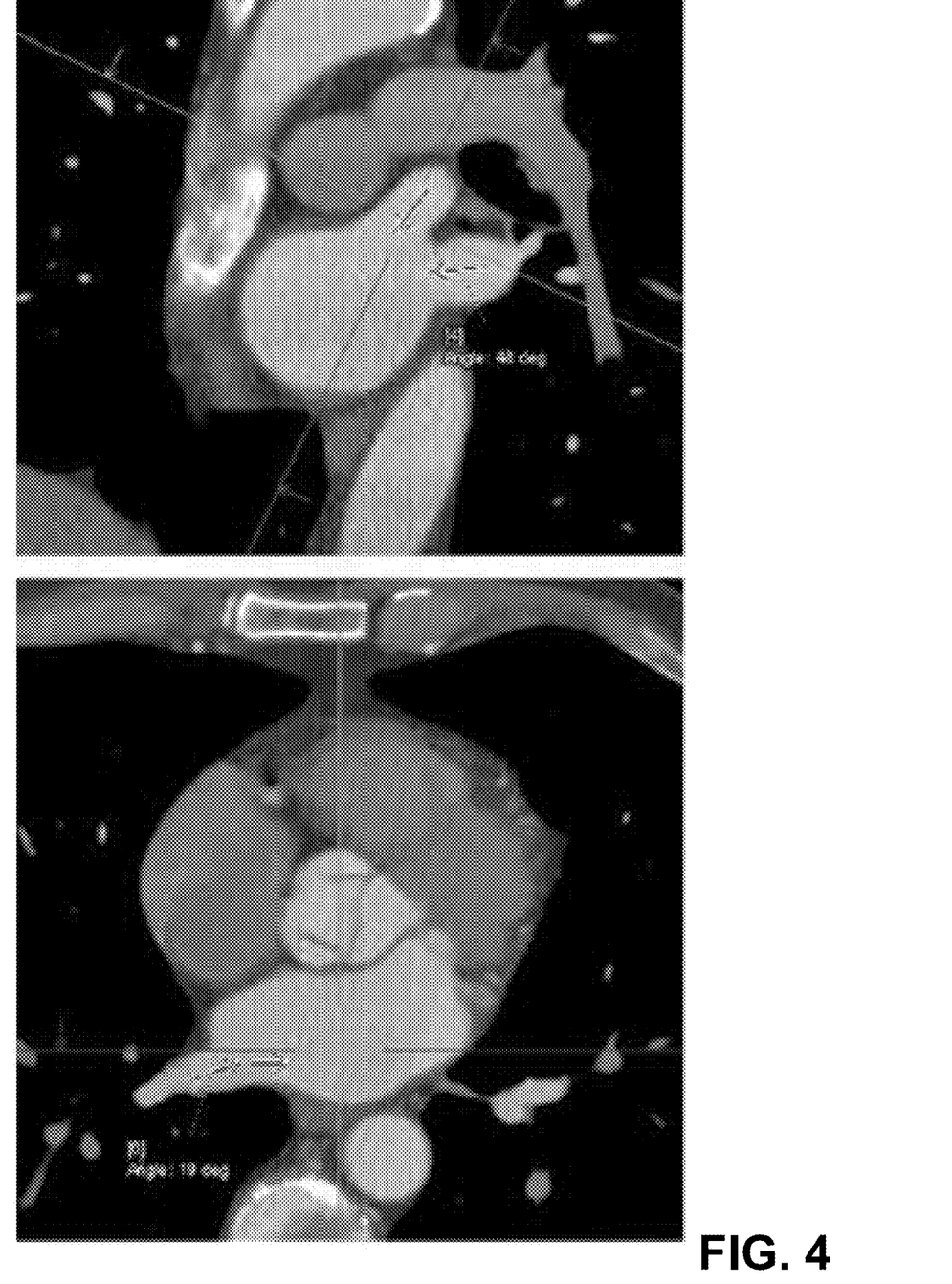
FIG. 4 illustrates a pair of CT (Computed Tomography) images indicating radiographic features considered for the example embodiment, according to various aspects discussed herein.

Referring to FIG. 4, illustrated is a pair of CT (Computed Tomography) images indicating radiographic features considered for the example embodiment, according to various aspects discussed herein.

Figure 5:
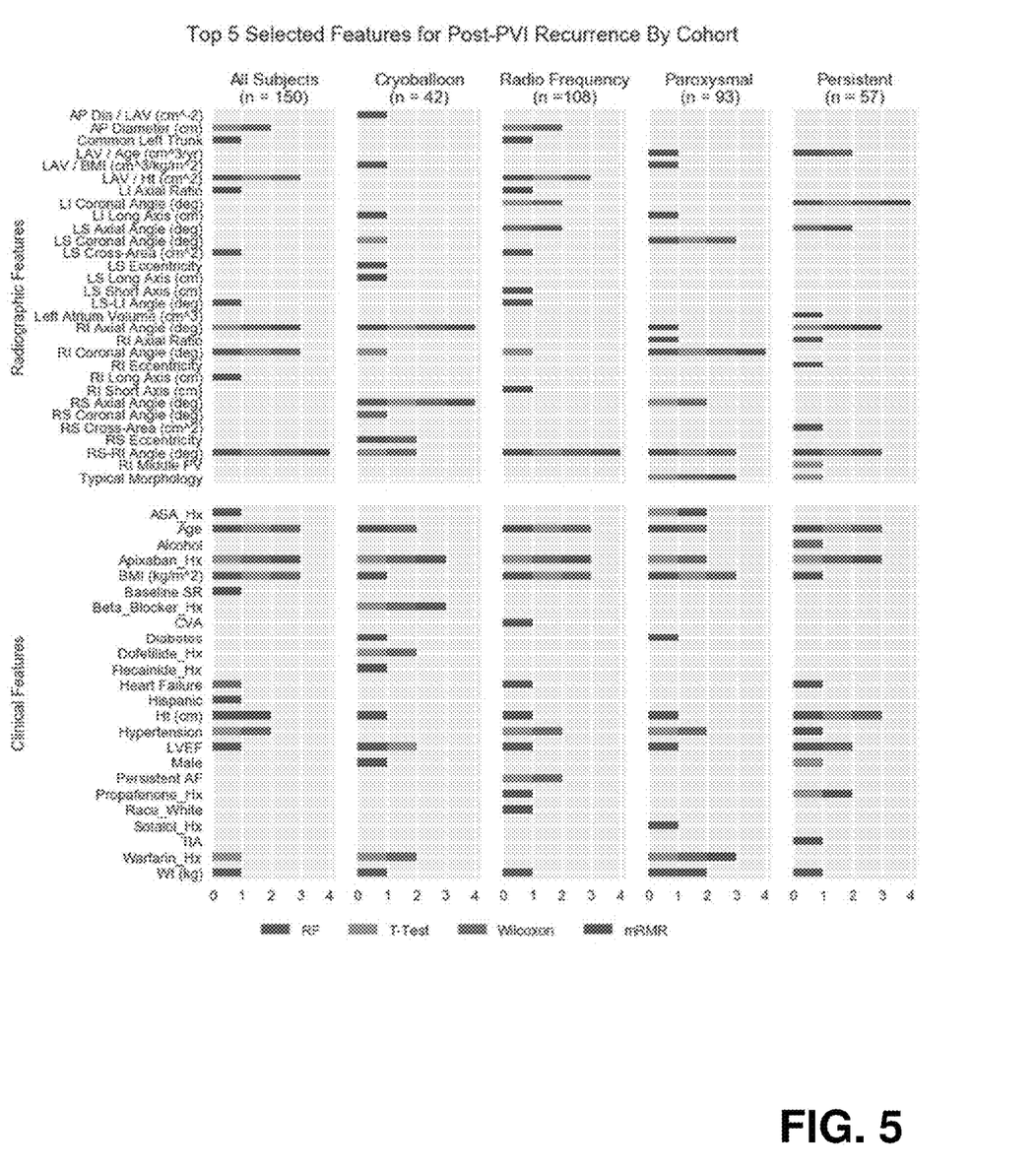
FIG. 5 illustrates a diagram showing radiographic and clinical features that were considered for the example embodiment, along with the five features of each type that were selected as the most distinguishing between recurrence vs. non-recurrence for AF after PVI, for each of four different feature selection algorithms or measures, and for cohorts including all subjects, subjects broken down by procedure (cryoballoon vs. radio frequency), and subjects broken down by AF type (paroxysmal vs. persistent), according to various embodiments discussed herein.

Referring to FIG. 5, illustrated is a diagram showing radiographic and clinical features that were considered for the example embodiment, along with the five features of each type that were selected as the most distinguishing between recurrence vs. non-recurrence for AF after PVI, for each of four different feature selection algorithms or measures, and for cohorts including all subjects, subjects broken down by procedure (cryoballoon vs. radio frequency), and subjects broken down by AF type (paroxysmal vs. persistent), according to various embodiments discussed herein. The four different feature selection algorithms/measures considered were RF (Random Forest), t-test, Wilcoxon, and mRMR (minimum redundancy maximum relevance).

The radiographic features considered for the example embodiment comprised: (1) AP Dia/LAV (anterior-posterior diameter (of left atrium) divided by left atrial volume); (2) AP Diameter (anterior-posterior diameter (of left atrium)); (3) Common left trunk (presence of anatomic variant where left pulmonary veins join before entering the left atrium); (4) LAV/Age (left atrial volume divided by age); (5) LAV/BMI (left atrial volume divided by body mass index); (6) LAV/Ht (left atrial volume divided by height); (7) LI (left inferior pulmonary vein) axial ratio (ratio calculated by short and long axis of pulmonary vein cross section (how round the vein is in cross section)); (8) LI coronal angle (angle of entry of the pulmonary vein into the left atrium as seen on coronal plane of the CT image) in degrees; (9) LI long axis in cm; (10) LS (left superior pulmonary vein) axial angle (angle of entry of the pulmonary vein into the left atrium as seen on axial plane of the CT image) in degrees; (11) LS coronal angle in degrees; (12) LS cross-area (cross sectional area) in $cm^2$; (13) LS eccentricity (which is similar to axial ratio, but based on a different equation); (14) LS long axis in cm; (15) LS short axis in cm; (16) LS-LI angle (angle between the inferior and superior pulmonary veins on the left side of the atrium); (17) left atrium volume in $cm^3$; (18) RI (right inferior pulmonary vein) axial angle in degrees; (19) RI axial ratio; (20) RI coronal angle in degrees; (21) RI eccentricity; (22) RI long axis in cm; (23) RI short axis in cm; (24) RS (right superior pulmonary vein) axial angle in degrees; (25) RS coronal angle in degrees; (26) RS cross-area in $cm^2$; (27) RS eccentricity; (28) RS-RI angle (angle between the inferior and superior pulmonary veins on the right side of the atrium) in degrees; (29) Rt middle PV (presence of a right middle PV (anatomic variant where the vein enters the left atrium rather than the RS pulmonary vein)); and (30) typical morphology (absence of a common pulmonary vein trunk or a right middle vein).

The clinical features considered for the example embodiment comprised: (1) ASA_Hx (history of use of aspirin (acetyl salicylic acid)); (2) age; (3) alcohol; (4) apixaban_Hx (history of use of apixaban); (5) BMI (body mass index) in $kg/m^2$; (6) baseline SR (sinus rhythm vs atrial fibrillation on day of ablation therapy); (7) Beta_Blocker_Hx (history of use of beta blocker(s)); (8) CVA (stroke history); (9) diabetes; (10) Dofetilide_Hx (history of use of dofetilide); (11) Flecainide_Hx (history of use of Flecainide) (12) heart failure; (13) Hispanic; (14) height in cm; (15) hypertension; (16) LVEF (left ventricular ejection fraction); (17) male; (18) persistent AF (whether AF is persistent or paroxysmal); (19) Propafenone_Hx (history of use of propafenone); (20) Race_White; (21) Sotalol_Hx (history of use of sotalol); (22) TIA (history of transient ischemic attacks); (23) Warfarin_Hx (history of use of warfarin); and (24) weight in kg.

As can be seen in FIG. 5, the most distinguishing radiographic and clinical features varied to some degree by algorithm/measure and cohort. For the example embodiment, the 5 most distinguishing features were selected by Wilcoxon rank-sum and used to train a support vector machine classifier in a 3-fold cross-validation setting. Ability to predict recurrence was assessed by area under the receiver operating characteristic curve (AUC) among all patients and the predictive ability including clinical features was investigated similarly.

Figure 6:
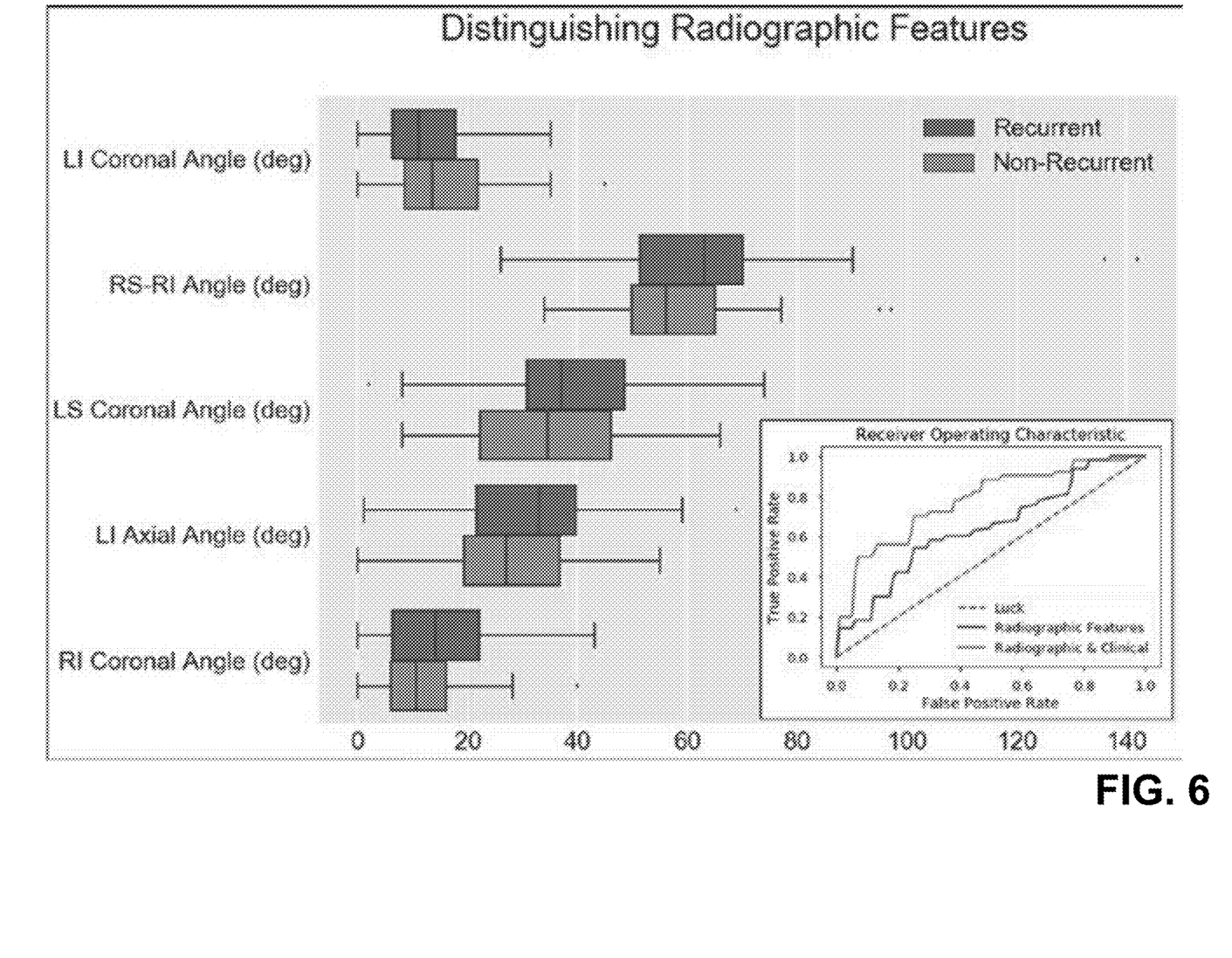
FIG. 6 illustrates a diagram showing five radiographic features employed in the example embodiment, along with AUC (Area under Receiver Operating Characteristic Curve) for an embodiment employing just radiographic features and an embodiment employing radiographic and clinical features, according to various embodiments discussed herein.

Referring to FIG. 6, illustrated is a diagram showing five radiographic features employed in the example embodiment, along with AUC (Area under Receiver Operating Characteristic Curve) for an embodiment employing just radiographic features and an embodiment employing radiographic and clinical features, according to various embodiments discussed herein.

In the example embodiment, the most distinguishing radiographic features comprised the angle between right pulmonary veins (p=0.063) and angle of left inferior pulmonary vein entry into the left atrium (p=0.060), among others (e.g., AP diameter, LAV/Ht, RI axial angle, RI coronal angle, RS-RI angle, LI coronal angle, LS coronal angle, LI axial angle, etc.). The radiographic features effectively predicted recurrence of AF within 1 year of PVI (AUC=0.65±0.03) and inclusion of clinical features further improved performance (AUC=0.77±0.02). Distinguishing clinical features employed by the example embodiment comprised age (p<0.001), BMI (p=0.005), left ventricular ejection fraction (p=0.014), history of hypertension (p=0.016), NYHA (New York Heart Association) class of I or greater (p=0.016), and use of apixaban (p=0.016).

As demonstrated by the example embodiments, various embodiments can facilitate prediction of recurrence of AF after endovascular treatment based on radiographic features comprising pulmonary vein morphology, as shown in CT images. The ability to identify patients likely to have recurrent AF based on CT morphometric features can provide a pre-treatment indicator of response and anatomic features that can be targeted.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to determination of recurrence or non-recurrence of atrial fibrillation after endovascular pulmonary vein isolation (PVI) based on radiographic and clinical features are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 7:
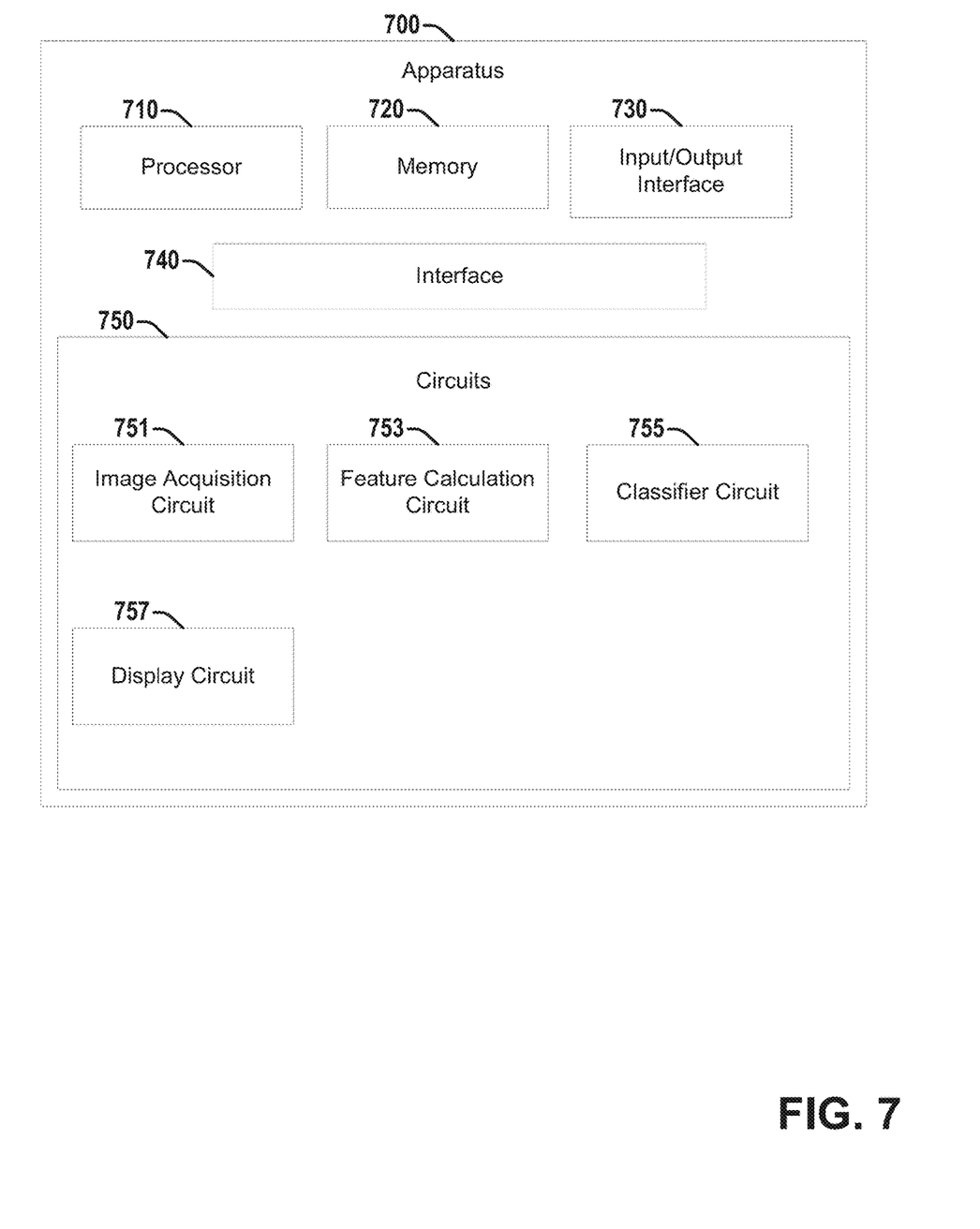
FIG. 7 illustrates a diagram of a first example apparatus that can facilitate prediction of recurrence of AF after PVI, according to various embodiments discussed herein.

Referring to FIG. 7, illustrated is a diagram of a first example apparatus 700 that can facilitate prediction of recurrence of AF after PVI based on radiographic and/or clinical features, according to various embodiments discussed herein. Apparatus 700 can be configured to perform various techniques discussed herein, for example, training a classifier (e.g., support vector machine, etc.) based on training data to determine probability of recurrence of AF after PVI based on at least one of radiographic or clinical features, and/or employing such a trained classifier to generate a prognosis of recurrence or non-recurrence based on a cardiac CT image of a patient, alone or in combination with clinical features. Apparatus 700 comprises a processor 710. Apparatus 700 also comprises a memory 720. Processor 710 can, in various embodiments, comprise circuitry such as, but not limited to, one or more single-core or multi-core processors. Processor 710 can include any combination of general-purpose processors and dedicated processors (e.g., graphics processors, application processors, etc.). The processor(s) can be coupled with and/or can comprise memory (e.g., memory 720) or storage and can be configured to execute instructions stored in the memory 720 or storage to enable various apparatus, applications, or operating systems to perform operations and/or methods discussed herein. Memory 720 can be configured to store one or more radiological cardiac images (e.g., CT, MRI, PET, SPECT, ultrasound, etc.). Each of the radiological image(s) can have a plurality of pixels, each pixel having an associated intensity. In some embodiments, memory 720 can store a training set of images (e.g., comprising radiological cardiac images showing radiographic features, along with a known recurrence or not of AF post PVI) for training a classifier (e.g., support vector machine, etc.) to determine a prognosis for a patient with AF after potential PVI, while in the same or other embodiments, memory 720 can store a radiological cardiac image of a patient for whom a prognosis is to be determined. Memory 720 can be further configured to store one or more clinical features associated with the patient.

Apparatus 700 also comprises an input/output (I/O) interface 730 (e.g., associated with one or more I/O devices), a set of circuits 750, and an interface 740 that connects the processor 710, the memory 720, the I/O interface 730, and the set of circuits 750. I/O interface 730 can be configured to transfer data between memory 720, processor 710, circuits 750, and external devices, for example, a medical imaging device such as a CT (etc.) system or apparatus.

The set of circuits 750 can comprise an image acquisition circuit 751, an feature calculation circuit 753, a classifier circuit 755, and a display circuit 757. Image acquisition circuit 751 is configured to access one or more radiological cardiac images (e.g., a training set of images, or an image of a patient for whom a prognosis is to be determined). Accessing the radiological image(s) can comprise accessing radiological image(s) stored in memory 720. In one embodiment, accessing the radiological image(s) can include accessing radiological image(s) stored in a data storage device, including a hard disk drive, a solid state device, a tape drive, or accessing radiological image(s) over a local area network. Accessing the radiological image(s) can comprise acquiring electronic data, reading from a computer file, receiving a computer file, reading from a computer memory, or other computerized activity not practically performed in the human mind.

In various embodiments, feature calculation circuit 753 is configured to determine values for one or more radiographic features based on a radiological cardiac image (e.g., cardiac CT image, etc.). In various embodiments, the one or more radiographic features can comprise the M most distinguishing features, as determined via one of a variety of algorithms or measures (e.g., RF, t-test, Wilcoxon, mRMR, etc.). The radiological cardiac image can be a member of a training dataset for which a prognosis is known, wherein the values for the one or more radiographic features can be used for training a classifier (e.g., SVM, etc.) implemented by classifier circuit 755. In the same or other embodiments, the radiological cardiac image can be a member of a testing dataset for which a prognosis is to be determined by classifier circuit 755 to determine the ability of the classifier of classifier circuit 755 to distinguish between recurrent and non-recurrent cases. Alternatively, in the same or other embodiments, the radiological cardiac image can be an image of a patient for whom a prognosis of recurrence or non-recurrence of AF after PVI is to be determined by the classifier of classifier circuit 755.

In various embodiments, classifier circuit 755 can receive values for one or more radiographic features of a radiological cardiac image from feature calculation circuit 753. In some embodiments, the received values of the features can correspond to an image of a training dataset, and the classifier of classifier circuit 755 can be trained based on the values and a known prognosis associated with the image (and optionally, value(s) of associated clinical feature(s)). In the same or other embodiments, the received values of the features can correspond to an image of a testing dataset or of a patient for whom a prognosis is to be generated, and the classifier of classifier circuit 755 can generate a prognosis based on the values of the radiographic feature(s), and optionally, value(s) of one or more associated clinical features.

Display circuit 757 is configured to output or display the prognosis determined by classifier circuit 755. In various embodiments, the prognosis can comprise one or more of a most likely prognostic outcome (e.g., as determined based on the radiological and/or clinical features, etc.) such as recurrence or non-recurrence; a probability or confidence associated with a most likely prognostic outcome; and/or associated probabilities/confidences associated with each of a plurality of prognostic outcomes (e.g., recurrence, non-recurrence, etc.).

Figure 8:
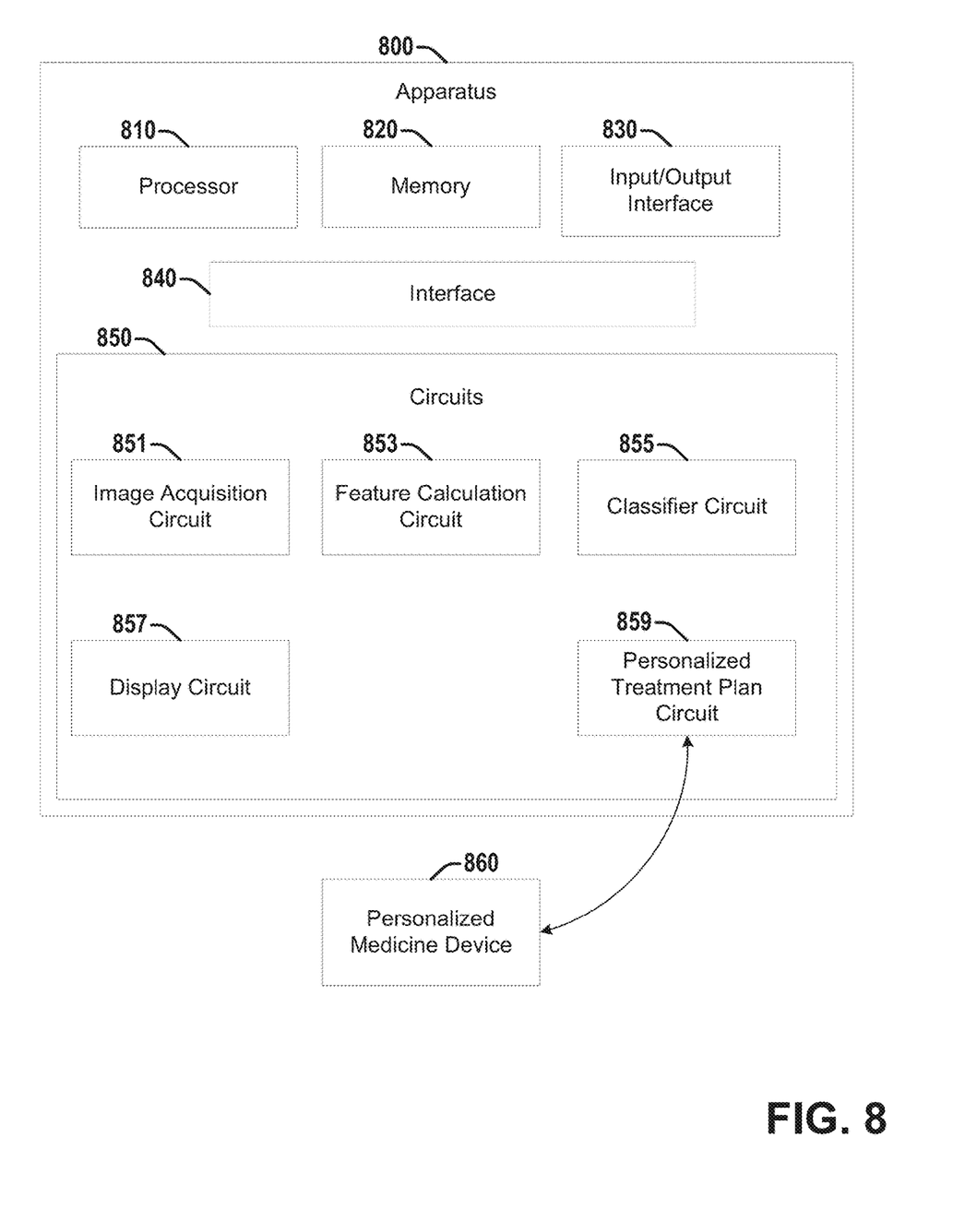
FIG. 8 illustrates a diagram of a second example apparatus that can facilitate prediction of recurrence of AF after PVI, according to various embodiments discussed herein.

Referring to FIG. 8, illustrated is a diagram of a second example apparatus 800 that can facilitate prediction of recurrence of AF after PVI, according to various embodiments discussed herein. Example apparatus 800 is similar to the example apparatus of FIG. 8 (e.g., with elements 810-857 corresponding to elements 710-757, etc.), but comprises additional details and elements. Apparatus 800 can also comprise personalized treatment plan circuit 859. Personalized treatment plan circuit 859 can be configured to generate a personalized treatment plan based, at least in part, on a prognosis obtained from classifier circuit 855 or display circuit 857. Personalized treatment plan circuit 859 can be configured to generate a personalized treatment plan for the patient of whom the radiological cardiac image was acquired based, at least in part, on the prognosis derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment (e.g., PVI, etc.), may suggest a pharmaceutical agent dosage or schedule, and/or other treatments.

Apparatus 800 can further comprise personalized medicine device 860. Apparatus 800 can be configured to provide the prognosis, personalized treatment plan, or other data to personalized medicine device 860. Personalized medicine device 860 may be, for example, a computer assisted diagnosis (CADx) system or other type of personalized medicine device that can be used to facilitate the prediction of disease recurrence. In one embodiment, personalized treatment plan circuit 859 can control personalized medicine device 860 to display the prognosis, personalized treatment plan, or other data on a computer monitor, a smartphone display, a tablet display, or other displays.

Examples herein can include subject matter such as an apparatus, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a radiological cardiac image associated with a patient, wherein the radiological cardiac image comprises a plurality of pixels, wherein each pixel of the plurality of pixels has an associated intensity; extracting, from the radiological cardiac image, for each radiographic feature of M radiographic features, an associated value for that radiographic feature based on the radiological cardiac image, wherein M is a positive integer; providing to a machine learning classifier, for each radiographic feature of the M radiographic features, the associated value for that radiographic feature; generating, via the machine learning classifier, a prognosis for atrial fibrillation (AF) after pulmonary vein isolation (PVI), based at least in part on the associated values for each radiographic feature of the M radiographic features, wherein the prognosis comprises a determination of one of recurrence or non-recurrence; and displaying the generated prognosis for AF after PVI.

Example 2 comprises the subject matter of any variation of any of example(s) 1, wherein the radiological cardiac image is a CT (Computed Tomography) image.

Example 3 comprises the subject matter of any variation of any of example(s) 1-2, wherein the machine learning classifier is a support vector machine (SVM).

Example 4 comprises the subject matter of any variation of any of example(s) 1-3, wherein the operations further comprise providing to the machine learning classifier, for each clinical feature of N clinical features, an associated value for that clinical feature, wherein N is a positive integer, and wherein generating the prognosis for AF after PVI is based at least in part on the associated values for each clinical feature of the N clinical features.

Example 5 comprises the subject matter of any variation of any of example(s) 4, wherein the N clinical features comprise the N most distinguishing clinical features as determined via one of a random forest (RF) algorithm, a t-test, a Wilcoxon rank-sum algorithm, or a minimum redundancy maximum relevance (mRMR) algorithm.

Example 6 comprises the subject matter of any variation of any of example(s) 4-5, wherein N is 5.

Example 7 comprises the subject matter of any variation of any of example(s) 4-6, wherein the N clinical features comprise one or more of age, body mass index (BMI), left ventricular ejection fraction (LVEF), history of hypertension, NYHA (New York Heart Association) class of I or greater, or use of apixaban.

Example 8 comprises the subject matter of any variation of any of example(s) 1-7, wherein the M radiographic features comprise the M most distinguishing radiographic features as determined via one of a random forest (RF) algorithm, a t-test, a Wilcoxon rank-sum algorithm, or a minimum redundancy maximum relevance (mRMR) algorithm.

Example 9 comprises the subject matter of any variation of any of example(s) 8, wherein M is 5.

Example 10 comprises the subject matter of any variation of any of example(s) 8-9, wherein the M radiographic features comprise one or more of a coronal angle of a left inferior pulmonary vein (LI), an angle between a right superior pulmonary vein (RS) and a right inferior pulmonary vein (RI), a coronal angle of a left superior pulmonary vein (LS), an axial angle of the LI, or a coronal angle of the RI.

Example 11 is an apparatus that facilitates generation of a prognosis in connection with a medical condition, the apparatus comprising: a processor; a memory configured to store a radiological cardiac image associated with a patient, wherein the radiological cardiac image comprises a plurality of pixels, wherein each pixel of the plurality of pixels has an associated intensity; an input/output (I/O) interface; a set of circuits; and an interface that connects the processor, the memory, the I/O interface, and the set of circuits, the set of circuits comprising: an image acquisition circuit configured to access the radiological cardiac image; a feature calculation circuit configured to calculate, for each of M radiographic features, an associated value of that radiographic feature for the radiological cardiac image, wherein M is a positive integer; a classifier circuit configured to: access, for each of the M radiographic features, the associated value of that radiographic feature; and generate, based at least in part on the associated values for each of the M radiographic features, a prognosis for the patient for atrial fibrillation (AF) after pulmonary vein isolation (PVI), wherein the prognosis comprises a determination of one of recurrence or non-recurrence; and a display circuit configured to output the prognosis for the patient associated with the radiological cardiac image.

Example 12 comprises the subject matter of any variation of any of example(s) 11, wherein the radiological cardiac image is a CT (Computed Tomography) image.

Example 13 comprises the subject matter of any variation of any of example(s) 11-12, wherein the machine learning classifier is a support vector machine (SVM).

Example 14 comprises the subject matter of any variation of any of example(s) 11-13, wherein the classifier circuit is further configured to access, for each clinical feature of N clinical features, an associated value for that clinical feature, wherein N is a positive integer, and wherein the classifier circuit is configured to generate the prognosis based at least in part on the associated values for each clinical feature of the N clinical features.

Example 15 comprises the subject matter of any variation of any of example(s) 14, wherein the N clinical features comprise the N most distinguishing clinical features as determined via one of a random forest (RF) algorithm, a t-test, a Wilcoxon rank-sum algorithm, or a minimum redundancy maximum relevance (mRMR) algorithm.

Example 16 comprises the subject matter of any variation of any of example(s) 14-15, wherein the N clinical features comprise one or more of age, body mass index (BMI), left ventricular ejection fraction (LVEF), history of hypertension, NYHA (New York Heart Association) class of I or greater, or use of apixaban.

Example 17 comprises the subject matter of any variation of any of example(s) 11-16, wherein the M radiographic features comprise the M most distinguishing radiographic features as determined via one of a random forest (RF) algorithm, a t-test, a Wilcoxon rank-sum algorithm, or a minimum redundancy maximum relevance (mRMR) algorithm.

Example 18 comprises the subject matter of any variation of any of example(s) 17, wherein the M radiographic features comprise one or more of a coronal angle of a left inferior pulmonary vein (LI), an angle between a right superior pulmonary vein (RS) and a right inferior pulmonary vein (RI), a coronal angle of a left superior pulmonary vein (LS), an axial angle of the LI, or a coronal angle of the RI.

Example 19 is a non-transitory computer-readable medium storing computer-executable instructions that, when executed, cause a processor to perform operations, comprising: accessing a training dataset of cardiac CT (Computed Tomography) images, wherein each cardiac CT (Computed Tomography) image of the plurality of cardiac CT (Computed Tomography) images comprises an associated plurality of pixels, wherein each pixel of the associated plurality of pixels has an associated intensity; determining, for each radiographic feature of M radiographic features, an associated value for that radiographic feature for each cardiac CT (Computed Tomography) image of the training dataset; accessing, for each clinical feature of N clinical features, an associated value for that clinical feature associated with each cardiac CT (Computed Tomography) image of the training dataset; and training a support vector machine (SVM) classifier based on the training dataset, the associated values for each radiographic feature of the M radiographic features for each cardiac CT image of the training dataset, the associated values for each clinical feature of the N clinical features associated with each cardiac CT image of the training dataset, and a known prognosis associated with each cardiac CT image of the training dataset.

Example 20 comprises the subject matter of any variation of any of example(s) 19, wherein the M radiographic features comprise the M most distinguishing radiographic features as determined via one of a random forest (RF) algorithm, a t-test, a Wilcoxon rank-sum algorithm, or a minimum redundancy maximum relevance (mRMR) algorithm, and wherein the N clinical features comprise the N most distinguishing clinical features as determined via one of the random forest (RF) algorithm, the t-test, the Wilcoxon rank-sum algorithm, or the minimum redundancy maximum relevance (mRMR) algorithm.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
  accessing a radiological cardiac image associated with a patient, wherein the radiological cardiac image comprises a plurality of pixels, wherein each pixel of the plurality of pixels has an associated intensity;
  obtaining M radiographic features from the radiological cardiac image, wherein the M radiographic features characterize a left atrium size of a heart and a pulmonary vein morphology and wherein M is a positive integer;

extracting, for each radiographic feature of the M radiographic features, an associated value for that radiographic feature based on the radiological cardiac image;

providing to a machine learning classifier, for each radiographic feature of the M radiographic features, the associated value for that radiographic feature;

generating, via the machine learning classifier, a prognosis for atrial fibrillation (AF) after pulmonary vein isolation (PVI), based on a subset of radiographic features of the M radiographic features, wherein the subset of radiographic features is smaller than the M radiographic features, wherein the prognosis comprises a determination of one of recurrence or non-recurrence, and wherein the subset of radiographic features comprise an angle between right pulmonary veins and an angle of left inferior pulmonary vein entry into a left atrium; and displaying the generated prognosis for AF after PVI.

2. The non-transitory computer-readable medium of claim 1, wherein the machine learning classifier is a support vector machine (SVM).

3. The non-transitory computer-readable medium of claim 1, wherein the operations further comprise providing to the machine learning classifier, for each clinical feature of N clinical features, an associated value for that clinical feature, wherein N is a positive integer, and wherein generating the prognosis for AF after PVI is based at least in part on the associated values for each clinical feature of the N clinical features including age, body mass index (BMI), left ventricular ejection fraction (LVEF), history of hypertension, NYHA (New York Heart Association) class of I or greater, and use of apixaban.

4. The non-transitory computer-readable medium of claim 3, wherein the N clinical features comprise the N most distinguishing clinical features as determined via one of a random forest (RF) algorithm, a t-test, a Wilcoxon rank-sum algorithm, or a minimum redundancy maximum relevance (mRMR) algorithm.

5. The non-transitory computer-readable medium of claim 3, wherein N is 5.

6. The non-transitory computer-readable medium of claim 1, wherein the M radiographic features characterize the left atrium size, the pulmonary vein morphology, and an angle of vein entry into a left atrium.

7. The non-transitory computer-readable medium of claim 1, wherein the subset of radiographic features comprise the most distinguishing radiographic features of the M radiographic features, the most distinguishing radiographic features including an angle between pulmonary veins.

8. The non-transitory computer-readable medium of claim 7, wherein the subset of radiographic features has 5 radiographic features.

9. The non-transitory computer-readable medium of claim 7, wherein the M radiographic features comprise one or more of a coronal angle of a left inferior pulmonary vein (LI), an angle between a right superior pulmonary vein (RS) and a right inferior pulmonary vein (RI), a coronal angle of a left superior pulmonary vein (LS), an axial angle of the LI, or a coronal angle of the RI.

10. An apparatus that facilitates generation of a prognosis in connection with a medical condition, the apparatus comprising:

a processor;

a memory configured to store a radiological cardiac image associated with a patient, wherein the radiological cardiac image comprises a plurality of pixels, wherein each pixel of the plurality of pixels has an associated intensity;

an input/output (I/O) interface;

a set of circuits; and an interface that connects the processor, the memory, the I/O interface, and the set of circuits, the set of circuits comprising:

an image acquisition circuit configured to access the radiological cardiac image;

a feature calculation circuit configured to:

obtain M radiographic features from the radiological cardiac image, wherein the M radiographic features characterize a left atrium size of a heart and a pulmonary vein morphology; and calculate, for each of the M radiographic features, an associated value of that radiographic feature for the radiological cardiac image, wherein M is a positive integer;

a classifier circuit configured to:

access, for each of the M radiographic features, the associated value of that radiographic feature; and generate a prognosis for the patient for atrial fibrillation (AF) after pulmonary vein isolation (PVI), based on a subset of radiographic features of the M radiographic features, wherein the subset of radiographic features is smaller than the M radiographic features, wherein the prognosis comprises a determination of one of recurrence or non-recurrence, and wherein the subset of radiographic features comprise an angle between right pulmonary veins and an angle of left inferior pulmonary vein entry into a left atrium; and a display circuit configured to output the prognosis for the patient associated with the radiological cardiac image.

11. The apparatus of claim 10, wherein the subset of radiographic features comprise the most distinguishing radiographic features of the M radiographic features, the most distinguishing radiographic features including an angle between pulmonary veins.

12. The apparatus of claim 10, wherein the classifier circuit is a support vector machine (SVM).

13. The apparatus of claim 10, wherein the classifier circuit is further configured to access, for each clinical feature of N clinical features, an associated value for that clinical feature, wherein N is a positive integer, and wherein the classifier circuit is configured to generate the prognosis based at least in part on the associated values for each clinical feature of the N clinical features.

14. The apparatus of claim 13, wherein the N clinical features comprise the N most distinguishing clinical features as determined via one of a random forest (RF) algorithm, a t-test, a Wilcoxon rank-sum algorithm, or a minimum redundancy maximum relevance (mRMR) algorithm.

15. The apparatus of claim 13, wherein the N clinical features comprise age, body mass index (BMI), left ventricular ejection fraction (LVEF), history of hypertension, NYHA (New York Heart Association) class of I or greater, and use of apixaban.

16. The apparatus of claim 10, wherein the M radiographic features comprise the M most distinguishing radiographic features as determined via one of a random forest (RF) algorithm, a t-test, a Wilcoxon rank-sum algorithm, or a minimum redundancy maximum relevance (mRMR) algorithm.

17. The apparatus of claim 16, wherein the M radiographic features comprise one or more of a coronal angle of a left inferior pulmonary vein (LI), an angle between a right superior pulmonary vein (RS) and a right inferior pulmonary vein (RI), a coronal angle of a left superior pulmonary vein (LS), an axial angle of the LI, or a coronal angle of the RI.

18. A non-transitory computer-readable medium storing computer-executable instructions that, when executed, cause a processor to perform operations, comprising:
- accessing a radiological cardiac image associated with a heart of a patient;
- extracting a plurality of radiographic features from the radiological cardiac image, wherein the plurality of radiographic features characterize a left atrium size of the heart and a pulmonary vein morphology;
- providing the plurality of radiographic features to a machine learning classifier, wherein the machine learning classifier is configured to select a subset of the plurality of radiographic features that have a high correlation to recurrence of pulmonary vein isolation (PVI) for the patient; and
- generating, via the machine learning classifier, a prognosis for atrial fibrillation (AF) after PVI based on the subset of the plurality of radiographic features, wherein the prognosis comprises a determination of one of recurrence or non-recurrence of AF and wherein the subset of the plurality of radiographic features comprise an angle between right pulmonary veins and an angle of left inferior pulmonary vein entry into a left atrium.

19. The non-transitory computer-readable medium of claim 18, wherein the subset of the plurality of radiographic features comprise an angle between pulmonary veins.

20. The non-transitory computer-readable medium of claim 18, wherein the machine learning classifier is a support vector machine (SVM).

* * * * *